United States Patent [19]

Fowler

[11] 4,372,309

[45] Feb. 8, 1983

[54] MOISTURE ABSORBENT PAD

[75] Inventor: George B. Fowler, Worcester, England

[73] Assignee: Humanicare International Inc., New Brunswick, N.J.

[21] Appl. No.: 205,720

[22] Filed: Nov. 10, 1980

[30] Foreign Application Priority Data

Jul. 19, 1980 [GB] United Kingdom ................ 8023685

[51] Int. Cl.³ .......................................... A61F 13/16
[52] U.S. Cl. .................................. 128/284; 128/290 P
[58] Field of Search .................. 128/284, 287, 290 R, 128/290 W, 290 P, 156

[56] References Cited

U.S. PATENT DOCUMENTS

| | | | |
|---|---|---|---|
| 2,699,170 | 1/1955 | Morin | 128/287 |
| 2,896,627 | 7/1959 | Harwood | 128/290 R |
| 3,072,123 | 1/1963 | Davis | 128/284 |
| 3,183,910 | 5/1965 | Patterson | 128/290 R |
| 3,211,147 | 10/1965 | Pherson et al. | 128/284 |
| 3,315,676 | 4/1967 | Cooper | 128/287 |
| 3,344,789 | 10/1967 | Arnold et al. | 128/287 |
| 3,570,492 | 3/1971 | Bettencourt | 128/290 R |
| 3,666,611 | 5/1972 | Joa | 128/290 P |
| 3,769,978 | 11/1973 | DeNight et al. | 128/287 |
| 3,868,287 | 2/1975 | Lewyckyj | 128/287 |
| 3,938,522 | 2/1976 | Repke | 128/287 |
| 4,002,171 | 1/1977 | Taft | 128/284 |
| 4,027,672 | 6/1977 | Karami | 128/290 P |
| 4,041,949 | 8/1977 | Kozak | 128/287 |
| 4,055,184 | 10/1977 | Karami | 128/290 R |
| 4,085,754 | 4/1978 | Ness et al. | 128/290 W |
| 4,093,765 | 6/1978 | Schmidt | 128/290 R |

Primary Examiner—C. Fred Rosenbaum
Attorney, Agent, or Firm—James & Franklin

[57] ABSTRACT

A diffuser layer is interposed between layers of moisture absorbent material situated within a cover sheet. The diffuser layer comprises one or more tissue layers, each having a plurality of parallel corrugations to disperse moisture by capillary action. A compression seal is situated in the cover sheet separating two pad parts. The compression seal comprises first and second crimps, spaced by a section of the cover sheet. The ends of the pad parts are also sealed by crimping. The absorbent material is wood pulp impregnated with a starch polymer or an acrylic-based polymer to increase the absorbency thereof. An agent may be included in the pulp to prevent the biological degradation of urine. Substances may also be included in the pulp for absorbing volatile nitrogenous compounds and odors. In addition, a moisture or chemical sensitive indicator strip may be situated on the cover sheet.

11 Claims, 7 Drawing Figures

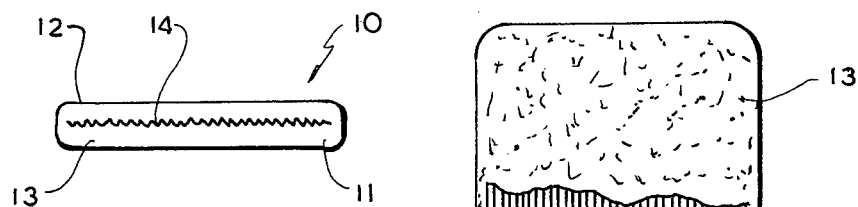
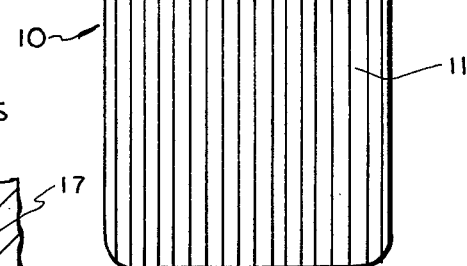
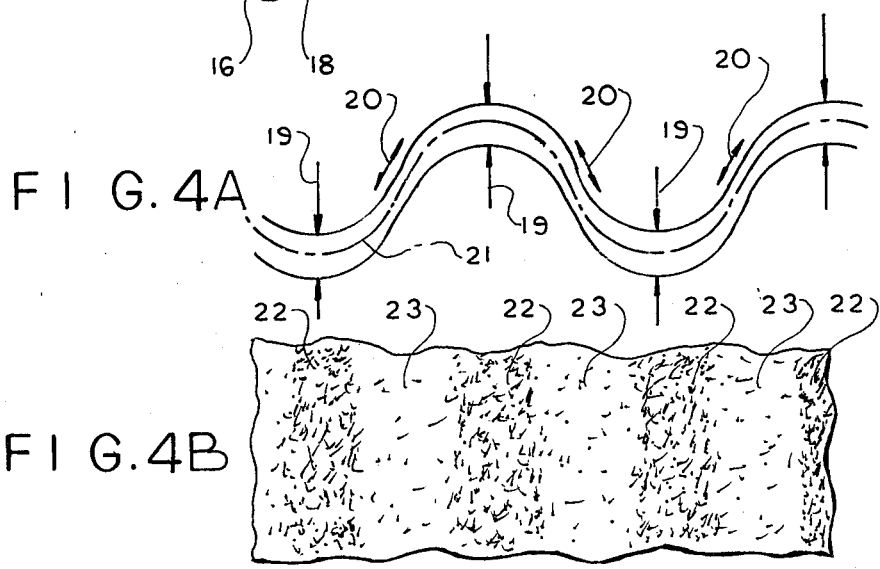

MOISTURE ABSORBENT PAD

BACKGROUND OF THE INVENTION

The present invention relates to moisture absorbent pads and, more particularly, to improvements in the construction of moisture absorbing pads to make same absorb more efficiently, more easily insertable into a pouch designed to hold same, and to certain substances designed for use therein to prevent odors and irritation caused by urine.

Moisture absorbent pads of the type to which the present invention relates are primarily designed for absorbing urine and are, thus, useful as incontinence pads, bed pads, or disposable diapers designed for use by infants. Although the moisture absorbent pad can be used for a number of different applications, the pads to which the present invention relates are primarily designed for use as incontinence pads in conjunction with a garment, such as a brief, having a pouch designed to receive the pad therein. For this reason, the present invention will be described in conjunction with this type of pad. However, it is to be appreciated that the present invention is not limited to incontinence pads alone, but has wider-spread application and, therefore, references to incontinence pads in the specification should not be considered to be a limitation on the invention.

It has long been recognized that the full absorbent capacity of conventional moisture absorbent pads is rarely utilized because the distribution of liquid throughout the pad is usually such that the liquid migrates to the edges of the pad more quickly in certain directions than other directions. Various arrangements have been proposed to minimize this distribution imbalance by utilizing such expedients as barriers of reduced permeability or layers affording a preferential direction for liquid spread. However, none of these proposed solutions are entirely acceptable for reasons of performance, cost or production difficulties.

Incontinence pads, designed for use with incontinence garments such as pants or the like, are normally removable from the garment so that the used pad can be disposed of and the garment reused. For this purpose, the garment is provided with a pouch designed to receive the pad therein. Because such garments are often used by elderly or ill individuals, the ease with which the pad can be inserted into the garment is important. It is therefore desirable to construct the pad in such a manner as to facilitate insertion into the pouch of a garment, either by the wearer or, in the case of the ill or senile, by the person caring for the wearer.

Ease of removability is also important, but is additionally complicated because the pad is normally moisture laden when it is ready to be removed. It is necessary for the pad to have sufficient strength so as not to disintegrate as it is being pulled from the garment. In addition, it is distasteful for the individual removing the pad to have his hand come in contact with the urine saturated portions of the pad. It is therefore desirable to construct the pad in such a manner that it has sufficient structural integrity and can be removed without coming in contact with the urine-laden portions.

Since the moisture absorbent pads are often worn for extended periods of time after urine has been absorbed therein, odors caused by the urine can become a problem. In addition, persons with urinary tract infections may excrete volatile nitrogenous compounds in the urine. Such compounds would normally escape from the pad, causing an additional odor. It is therefore desirable to include, within the pad, compounds which either neutralize or mask odors.

In many instances, such as when the pads are used by infants or senile individuals, it is impossible for the person caring for the individual to ascertain whether or not the pad has absorbed urine without touching same to see if it is moist, which process could be considered to be disagreeable. For this reason, it would be desirable to incorporate a moisture indicator on a visible portion of the pad such that one could tell at a glance whether the pad need be removed or not. Moreover, in certain applications, it is desirable to incorporate on the pad a means for visually indicating the presence or absence of certain chemicals in the urine. For instance, a test strip of the type which diabetics utilize to test for the presence of sugar could be incorporated on the pad.

It is, therefore, a prime object of the present invention to provide a moisture absorbent pad having improved moisture absorbent properties.

It is another object of the present invention to provide a moisture absorbent pad wherein the moisture is more uniformly diffused throughout the pad.

It is another object of the present invention to provide a moisture absorbent pad having a corrugated diffuser layer which more uniformly distributes moisture by means of capillary action.

It is another object of the present invention to provide a moisture absorbent pad wherein the absorbent material therein has increased absorbency properties.

It is a further object of the present invention to provide a moisture absorbent pad, the construction of which facilitates the insertion of same into a pouch.

It is a further object of the present invention to provide a moisture absorbent pad which may be removed without coming in contact with the moisture laden portions thereof.

It is another object of the present invention to provide a moisture absorbent pad which comprises two parts such that same can be used either in single or double strength.

It is a further object of the present invention to provide a moisture absorbent pad where the parts are connected by means of a compression seal in the cover sheet.

It is a further object of the present invention to provide a moisture absorbent pad which contains a bacterial static agent for preventing the biological degradation of urine.

It is another object of the present invention to provide a moisture absorbent pad including a substance for absorbing volatile nitrogenous compounds in the urine.

It is another object of the present invention to provide a moisture absorbent pad which has substances therein to neutralize or mask odor.

In accordance with one aspect of the present invention, a moisture absorbent pad is provided comprising a cover, first and second layers of moisture absorbent material situated within and enclosed by the cover, and a moisture diffuser layer situated between the absorbent material layers. The diffuser layer comprises a plurality of corrugations. The corrugations are situated in substantially the same direction.

The corrugations comprise alternating compressed and stretched zones. The density of the compressed zones being approximately 30% and, preferably, 50% less than the density of the stretched zones.

The diffuser layer may comprise a corrugated tissue and, preferably, comprises a plurality of corrugated tissue sheets. When a plurality of sheets are used, the corrugations in each sheet are aligned. The absorbent material comprises wood pulp impregnated either with a starch polymer or an acrylic based polymer, in order to increase the absorbency thereof.

The cover preferably comprises a non-woven material. The non-woven material may be rayon or similar material.

In accordance with another aspect of the present invention, a moisture absorbent pad is provided comprising a cover sheet, first and second spaced moisture absorbent parts situated within the cover sheet and means for operably connecting the parts. The connecting means comprises a compression seal in the cover sheet situated between the parts.

The connecting means preferably comprises first and second crimps, separated by a section of the cover sheet. In addition, compression seals are located at each of the non-connected ends of the parts. The compression seals provide structural rigidity to the pad to facilitate insertion and removal thereof. In addition, the compression seals provide a portion of the pad which is not moisture absorbent and may be grasped upon removal such that the individual's hands do not come in contact with the moisture-laden portions of the pad. Still further, because of the separate parts and the movable connection therebetween, the pad can be folded to be used as a double strength pad, spread out and used as tandem single pad parts, or severed between the central crimps and used as a single pad.

In accordance with another aspect of the present invention, a moisture absorbent pad is provided, comprising a cover sheet and moisture absorbent material enclosed by the cover sheet. The material includes a bacterial static agent for preventing the biological degradation of urine. The agent prevents the formation of ammonia and amines, as well as the growth of species b. ammoniagenes. Thus, the substance acts to prevent or neutralize odors which would normally be created.

In accordance with another aspect of the present invention, a moisture absorbent pad is provided comprising a cover sheet and moisture absorbing material enclosed by the cover sheet. The material includes a substance for absorbing volatile nitrogenous compounds. Such a substance may be boric acid or citric acid, and is solid in the normal state.

In accordance with another object of the present invention, a moisture absorbent pad comprising a cover sheet, a moisture absorbent material enclosed by the cover sheet, and moisture-sensitive indicating means situated on the cover sheet is provided. The moisture-sensitive indicating means may be in the form of a strip situated along the center line of the cover material. Alternatively, a chemical indicating strip may be substituted for the moisture-sensitive strip to indicate the presence or absence of certain chemical levels in the urine.

To these and such other objects as may hereinafter appear, the present invention relates to a moisture absorbent pad, as described in detail in the following specification, and recited in the annexed claims, taken together with the accompanying drawings, wherein like numerals refer to like parts and in which:

FIG. 1 is a partial cut-away plan view of the pad of the present invention, showing the internal construction thereof;

FIG. 2 is a cross-sectional view, taken along line 2—2 of FIG. 1;

FIG. 3 is a fragmentary cross-sectional view illustrating the form of the rollers used in the production of the diffuser layer;

FIGS. 4A and 4B are idealized diagrams illustrating the formation and structure of the diffuser layer, respectively;

Figure 5:
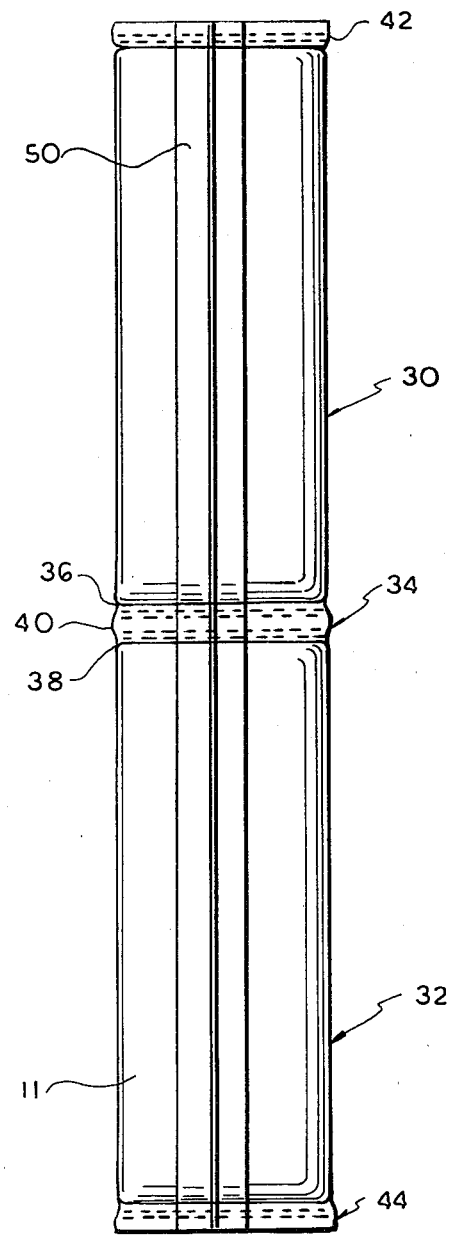
FIG. 5 is a plan view of a two-part absorbent pad, in accordance with the present invention; and, FIG. 6 is a side view of the two-part pad illustrated in FIG. 5.

The first aspect of the present invention relates to the construction of the pad which permits uniform distribution of the liquid throughout the pad so as to more efficiently utilize same, thereby permitting the absorption of a greater amount of liquid. In accordance with this aspect of the invention, the pad includes, between layers of absorbent material, at least one diffuser layer comprising one or a plurality of sheets of tissue which have been corrugated by passing same between a pair of matching grooved rollers to form corrugations having a pitch of the order of one millimeter, with the density of the tissue varying at least 30% across the width of each corrugation.

Such corrugated tissue is simple to manufacture, can be handled quite easily by conventional machinery on which absorbent pads are produced, and provides a strong wicking or capillary action longitudinally of the corrugations. Thus, if the corrugations are arranged longitudinally in an elongated rectangular pad, the rate of diffusion of liquid from the center of the pad towards its longitudinal extremities is greatly enhanced, with the result that in the time it takes liquid to spread to the lateral edges of the pad, the liquid will spread much further in the longitudinal direction, than would be the case without the diffuser layer. In this way, a greater proportion of the absorbent material is effectively utilized in absorbing the liquid before the pad becomes unacceptable to the user.

The diffuser layer can be manufactured by drawing off crepe tissue from a roll of stock and passing it between grooved rollers which form longitudinal corrugations in the tissue and the corrugated tissue can then be fed directly between two webs of absorbent material in a continuous operation.

Most conveniently, in practice, the material which is fed between the rollers comprises multi-ply, creped tissue so that the diffuser layer thus produced consists of a plurality of piles or sheets in which the corrugations are fully in register. However, a single-ply of creped tissue, of relatively greater width, may be passed between such rollers and, thereafter, folded upon itself several times so as to form a multi-ply layer in which the corrugations in individual sheets are not exactly in registration with one another.

In passing the tissue between the corrugated rollers, the tissue is stretched laterally at a series of localized positions across its width, with the result that the lateral coherence of the tissue is substantially disrupted and the resulting product consists of a plurality of longitudinally extending zones of differing density. In accordance with the invention, the density variation is at least 30% and, preferably, approximately 50%.

By this rolling/stretching process, the lateral strength of the tissue is also reduced by a similar factor, as compared with the untreated tissue, because the zones of reduced density afford lines of weakness and, ultimately, if the degree of stretching is sufficient, the original, coherent tissue is effectively reduced to a number of strands which barely cohere to one another. Thus, the diffuser layer formed in this way not only is highly efficient in promoting preferential diffusion of liquid in a desired direction, it is also readily disruptable so that the use of this layer does not impede disposal of the used pad by toilet flushing.

FIGS. 1 through 4 illustrate this aspect of the invention. As shown in FIGS. 1 and 2, a typical absorbent pad 10 includes a non-woven outer cover 11 made of rayon or other similar fabric, and two layers 12 and 13 of suitable absorbent material such as flocked wood pulp or the like. In order to increase its absorbency, the absorbent material which comprises layers 12 and 13 may be impregnated with a starch polymer or an acrylic based polymer.

Layers 12 and 13 of absorbent material are separated by a diffuser layer 14. Diffuser layer 14 comprises one or a plurality of sheets of creped tissue which has been corrugated by passage between a pair of matching rollers. The number of sheets may typically be between four and eight, although greater or smaller numbers may be utilized as appropriate for different types of pads. Likewise, although the illustrated embodiment includes a single diffuser layer 14 between two absorbent layers 12 and 13, the number of diffuser layers and absorbent layers may be varied, as necessary.

FIG. 3 illustrates a pair of matching rollers 15 and 16 formed with circumferentially extending grooves 17 and 18 which preferably have a pitch of approximately one millimeter. However, the pitch of the grooves may vary between about 0.5 millimeter and 2 millimeters, and still function acceptably. In addition, the grooves are provided with a peak-to-trough depth of a dimension which is similar to the pitch thereof.

As the creped tissue is drawn between the rollers, it is gripped and somewhat compressed at the point indicated by the arrows 19 in FIG. 4A between the troughs of one roller and the peaks of the other. The tissue is, thus, stretched as indicated by the double-headed arrows 20 between the points at which it is gripped. This is because the distance between the peaks of the grooves, as measured along the line 21 following the surface of the roller, exceeds the transverse spacing between the peaks as measured in the axial direction.

Thus, as seen in FIG. 4B, the multi-ply creped tissue material is slightly compressed in a plurality of longitudinally extending zones 22 where it is gripped between the rollers and simultaneously stretched in the intermediate zones 23. The corrugations are so dimensioned that the density of the material in zones 23 is at least 30% less than in the zones 22 and, preferably, 50% less or thereabout. In this way, the lateral cohesion of the creped tissue layer is reduced by a similar factor, as compared with the untreated tissue.

The corrugated material provides a strong capillary effect in the longitudinal direction, but the zones of weakness 23 serve to restrict the quantity of liquid which flows in the transverse direction. Thus, the multiply corrugated crepe tissue, in accordance with the present invention, forms a very efficient diffuser layer which promotes distribution of liquid in the lengthwise direction and, yet, it can be manufactured simply and economically from reliably available materials, without requiring expensive or complicated equipment.

Figure 6:
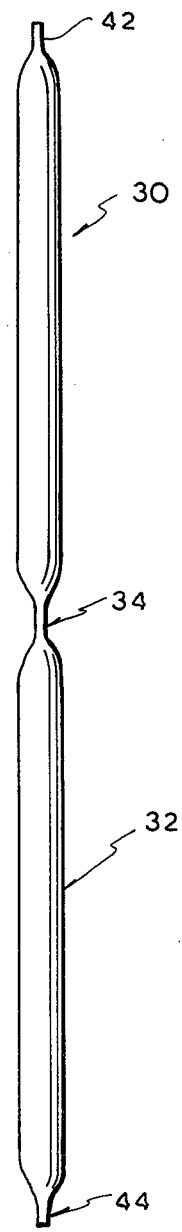

A second aspect of the present invention is illustrated in FIGS. 5 and 6, which show a plan view of a moisture absorbent pad which includes a cover sheet 11 and first and second spaced moisture absorbent parts 30, 32. Parts 30 and 32 are operably connected by means of a compression seal, generally designated 34. Seal 34 comprises a pair of hard or solid crimps 36, 38 which have a portion 40 of the cover sheet interposed therebetween so as to form a flexible joint.

At the non-connected ends of parts 30 and 32 are situated additional hard or solid crimps 42, 44, respectively. Each of the crimps 36, 38, 42 and 44 preferably comprise two rows, each containing a plurality of openings separated by aggregated material so as to form a relatively rigid crimp.

An incontinence garment is provided with an internal pouch designed to receive a pad therein. The central seal 34 permits the pad to be folded along cover material 40 between central crimps 36 and 37 such that part 30 and part 32 are substantially in face-to-face relationship, if a double layer is desired. Holding the pad by the central seal 34, insertion of the double-strength pad into the pouch is facilitated. After the pad has been used and is thus moisture laden, the pad can be extracted from the pouch by grabbing the central seal (which is not moisture laden) and pulling outwardly. Since the seal is not moisture absorbent, grasping the pad in this manner assures that the individual's hands will not come in contact with the moisture-laden portions of the pad. The pad can be used in a single layer in a similar manner simply by severing cover sheet 11 at 40 to create two separate pads, or both pad parts can be used in the unfolded state, so as to cover a greater area, by manipulating the end crimps 42 or 44, as described.

It should also be appreciated that the crimp structure illustrated in FIGS. 5 and 6 also substantially enhances the structural strength of the pad, thereby preventing deterioration thereof when same is saturated by liquid. It should also be noted that parts 30 and 32 may contain flocked wood pulp impregnated with starch polymer or acrylic based polymers in order to increase the absorbency thereof. Still further, a diffuser layer, as described above, may be utilized in each of the parts 30 and 32 to enhance the uniformity of distribution of the liquid throughout same and, therefore, increase the overall absorbency thereof. In this case, the corrugations are situated substantially perpendicular to the central seal 34.

In accordance with another aspect of the present invention, the flocked wood pulp absorbent material may have added thereto any one of a number of known bacterial static agents for preventing the biological degradation of urine. Such agents prevent the growth of bacteria of the species b. ammoniagenes and, therefore, prevent the formation of ammonia and amines by the biological degradation of urea, creatine and creatinine.

In addition, the use of a weak acid, which is solid in its normal state, as an additive to the moisture absorbent material will prevent any volatile nitrogenous compounds from escaping, if they are present in the excreted urine, due to a urinary tract infection. Examples of acids which may be useful for this purpose are boric and citric acids.

Moreover, certain well known deodorizing agents, urine neutralizing agents or odor masking agents can be used in order to prevent odors from emanating from the pad. Such agents may conveniently be situated in the moisture absorbent material.

FIG. 5 shows a moisture-sensitive indicator means in the form of a strip of material 50 situated along the center line of the cover material 11 of the pad 30, 32. The chemicals on the strip are designed so as to change color indicating that the pad has absorbed moisture. Such a strip is particularly useful when the pads are utilized by infants or senile individuals and permits one to ascertain the state of the pad without the necessity of touching same.

It is also possible to replace the moisture sensitive indicator strip 50 with a chemical test strip, such as is commonly used to test for the presence of sugar in urine by diabetics. The use of such a strip will automatically alert the user to the presence of any unusual levels of chemicals in the urine.

It will now be appreciated that the present invention relates to a moisture absorbing pad which utilizes a diffuser layer within the moisture absorbent material to uniformly distribute moisture throughout, thereby increasing the overall absorbency of the pad. In addition, certain polymers can be added to the moisture absorbent material to make same more absorbent. Further, the present invention relates to a pad structure which comprises two parts flexibly connected together by a central double crimp to enhance the structural rigidity of the pad and to facilitate insertion thereof into a pouch. Other aspects of the invention relate to the use of certain chemicals in the moisture absorbent material to prevent the growth of bacteria, prevent the escape of volatile nitrogenous compounds, neutralize or mask odor. Indicator strips may also be used on the cover sheets.

While only a limited number of preferred embodiments of the present invention have been disclosed herein for purposes of illustration, it is obvious that many variations and modifications could be made thereto. It is intended to cover all of these variations and modifications which fall within the scope of the present invention, as defined by the following claims:

I claim:

1. A pad of the type adapted to be situated in an incontinence garment or the like, said pad comprising first and second moisture absorbent parts and means for flexibly connecting said parts end-to-end, said connecting means being adapted to permit alignment of the parts in substantially face-to-face relation and comprising a substantially non-moisture absorbent graspable portion, said portion being accessible when said parts are in face-to-face relation and adapted to facilitate removal of the pad from a garment without substantial contact with said moisture absorbent parts.

2. The pad of claim 1, wherein said connecting means comprises first and second spaced crimps forming one end of each of said first and second parts and wherein said graspable portion is situated between said crimps.

3. The pad of claim 1, wherein said connecting means comprises a compression seal.

4. The pad of claim 1, wherein said pad further comprises a cover sheet into which said parts are situated in spaced relation, and wherein the portion of said cover sheet between said parts forms said connecting means.

5. The pad of claim 4, further comprising crimps in said cover sheet at the non-connected ends of said parts.

6. The pad of claim 1, wherein one of said parts comprises a moisture absorbent material enclosed by said cover sheet.

7. The pad of claim 6, wherein said absorbent material comprises wood pulp impregnated with starch polymer.

8. The pad of claim 6, wherein said absorbent material comprises wood pulp impregnated with an acrylic based polymer.

9. The pad of claim 6, wherein said one of said parts further comprises a diffuser layer situated within said absorbent material.

10. The pad of claim 9, wherein said diffusion layer has a plurality of corrugations therein.

11. The pad of claim 10, wherein said corrugations extend in a direction substantially perpendicular to said compression seal.

* * * * *